(12) United States Patent
Kolar

(10) Patent No.: US 11,076,789 B2
(45) Date of Patent: Aug. 3, 2021

(54) MEDICAL DATA COLLECTION SYSTEM AND METHOD OF USE THEREOF

(71) Applicant: Linet spol S.R.O., Slany (CZ)

(72) Inventor: Vladimir Kolar, Slany (CZ)

(73) Assignee: LINET SPOL. S.R.O, Slany (CZ)

( * ) Notice: Subject to any disclaimer, the term of this patent is extended or adjusted under 35 U.S.C. 154(b) by 91 days.

(21) Appl. No.: 16/304,160

(22) PCT Filed: Jun. 22, 2017

(86) PCT No.: PCT/CZ2017/000042
§ 371 (c)(1),
(2) Date: Nov. 22, 2018

(87) PCT Pub. No.: WO2017/220056
PCT Pub. Date: Dec. 28, 2017

(65) Prior Publication Data
US 2020/0187800 A1    Jun. 18, 2020

(30) Foreign Application Priority Data

Jun. 22, 2016 (CZ) ................................ CZ2016-366

(51) Int. Cl.
| A61B 5/24 | (2021.01) |
| A61B 5/024 | (2006.01) |
| A61B 5/0245 | (2006.01) |
| A61B 5/00 | (2006.01) |
| A61B 5/08 | (2006.01) |

(52) U.S. Cl.
CPC ............. *A61B 5/24* (2021.01); *A61B 5/0245* (2013.01); *A61B 5/02444* (2013.01); *A61B 5/7282* (2013.01); *A61B 5/024* (2013.01); *A61B 5/08* (2013.01); *A61B 2562/0247* (2013.01); *A61B 2562/164* (2013.01); *A61B 2562/182* (2013.01)

(58) Field of Classification Search
CPC . A61B 5/02444; A61B 5/0245; A61B 5/7282; A61B 2562/0247
See application file for complete search history.

(56) References Cited

U.S. PATENT DOCUMENTS

| 5,999,848 A * | 12/1999 | Gord .................. A61B 5/14865 607/2 |
| 8,536,988 B2 * | 9/2013 | Ritter .................... H04W 88/04 340/286.02 |

(Continued)

FOREIGN PATENT DOCUMENTS

WO    1999012607 A1    3/1999

OTHER PUBLICATIONS

WIPO, International Search Report, dated Oct. 16, 2017, in International Application No. PCT/CZ2017/000042, filed Jun. 22, 2017.
(Continued)

*Primary Examiner* — Jonathan T Kuo
(74) *Attorney, Agent, or Firm* — Thedford I. Hitaffer; Hitaffer & Hitaffer, PLLC

(57) ABSTRACT

The subject of the invention is a system for collecting medical data such as heart rate, breathing frequency, intracranial pressure, apnea and others, and method of use thereof. The present invention provides a unique way of collecting medical data, in particular in their acquisition from a plurality of measuring elements.

22 Claims, 3 Drawing Sheets

(56) References Cited

U.S. PATENT DOCUMENTS

| | | | |
|---|---|---|---|
| 8,538,625 B1* | 9/2013 | Lowchareonkul | B60K 35/00 |
| | | | 701/33.2 |
| 2009/0227965 A1* | 9/2009 | Wijesiriwardana | A61B 5/6815 |
| | | | 604/289 |
| 2011/0180709 A1* | 7/2011 | Craddock | G01J 1/46 |
| | | | 250/338.1 |
| 2011/0285516 A1* | 11/2011 | Ritter | H04W 88/04 |
| | | | 340/286.02 |
| 2012/0029304 A1* | 2/2012 | Medina | A61B 5/0002 |
| | | | 600/300 |
| 2014/0027589 A1 | 9/2014 | Muehlemann | |

OTHER PUBLICATIONS

WIPO, Written Opinion, dated Oct. 16, 2017 in International Application No. PCT/CZ2017/000042, filed Jun. 22, 2017.

\* cited by examiner

MEDICAL DATA COLLECTION SYSTEM AND METHOD OF USE THEREOF

CROSS-REFERENCE TO RELATED APPLICATIONS

This application, filed under 35 USC 371, is a United States National Stage Application of International Application No. PCT/CZ2017/000042, filed Jun. 22, 2017, which claims priority to CZ Application No. PV 2016-366, filed on Jun. 22, 2016, the disclosures of which are incorporated herein by reference.

TECHNICAL FIELD

The present invention relates to the field of medical data processing. More precisely, the present invention provides a new method of a medical data collection. Especially of medical data collection from a plurality of data acquisition elements.

BACKGROUND OF THE INVENTION

Remote monitoring has been used in health services for a long time. It is a very good tool for saving time and human resources. However, it is crucial to ensure that remote monitoring is carried out efficiently and mainly without errors.

There is currently a significant amount of apparatuses which are used in healthcare. The examples of these apparatuses are vital signs sensors, sensors of patient presence on bed, sensors monitoring bed status and the like. It is apparently a challenging task to achieve reliable data from multiple sensors of these medical apparatuses. Such apparatuses usually comprise several sensors which measure external mechanical or chemical states of their surroundings and by various electromechanical features provide measurement of the electrical physical quantities such as resistance, capacitance, amperage and so on. Measured data are sent as analog signal to a control unit. The analog signal has several disadvantages such as have low resistance to electromagnetic interference and the signal can be damaged, therefore it is necessary to use wires that protect the signal from such external disturbances. Furthermore, it is the state of the art of these devices, that the signal needs to be modulated in the sensor and demodulated prior to entering the control unit. Microprocessors are the most commonly used control units in such apparatuses.

The usual way of collecting information from set of sensors in such apparatuses utilizes classical topology of electrical circuit such as Y, T or star topology. In some cases, the star-mesh topology can be also used. However, said topology brings the need of using separate connection for each apparatus. Usually the signal wire (or more generally signal path) and the data signal path have to be used. This connection is quite expensive. It should be kept in mind that in typical healthcare application such as hospital beds, several apparatuses for measuring various states are provided. Firstly, vital functions of patients are to be monitored, such vital functions are most commonly heartbeat and respiration, although other such as apnea, intracranial pressure or peristalsis can be measured. These vital functions of the patient are most commonly measured by sensors based on capacity sensors or piezoelectric sensors. Other multiple sensor apparatuses are used in hospital beds, stretchers or chairs. Apparatuses indicate for example weight status of the patient, state of the bed, state of its actuators and so on.

There are various apparatuses in each room and most of them are remotely monitored from the nurses station. Therefore, in the case of star topology, every single apparatus has to be connected separately with the control unit of the measuring device, wherein the collected data are further sent to server or a readable monitor.

Prior art medical data collection systems do not provide safe collection of the measured data. Moreover, large number of hardware is needed for providing communication between sensors and control unit.

DESCRIPTION OF THE INVENTION

The above-mentioned disadvantages are partially overcome by the present invention of the medical data collection system. The system comprises a control unit and a plurality of measuring elements, wherein the measuring elements are connected in series via a data signal paths. A salient feature of the present invention is that the control unit further comprises a trigger and the trigger is connected to each measuring element via the trigger signal path. Preferably, the measuring element comprises piezoelectric and capacity sensor of vital functions. In a preferred embodiment, the measuring element includes the computing unit (23) of the measuring element.

The present invention also discloses a method of medical data collection in a data collection system. Said method introduces a set of logical operations which are necessary for data acquisition. First, the bigger initiates the data collection by transmitting the time-synchronizing impulse into each measuring element $A_k$. Second, the measuring element $A_N$ transmits its data package to the measuring element $A_{N-1}$ and measuring elements $A_2$-$A_{N-1}$ simultaneously receive the data packages from the measuring element $A_{k+1}$ and transmit their own data packages to the measuring element $A_{k-1}$. Simultaneously, the measuring element $A_1$ receives the data package from the measuring element $A_2$ and transmits its own data package to the control unit. In the next step, measuring elements $A_2$-$A_{N-2}$ simultaneously receive the data packages from the measuring element $A_{k+2}$ and transmit previously received data packages to the measuring element $A_{k-1}$. At the end of this process, the measuring element $A_1$ receives the data package from the measuring element $A_2$ and transmit previously received data package to the control unit, cascade receiving and transmitting of data packages continues until the data package from the measuring element $A_N$ is transmitted to the control unit by the measuring element $A_1$.

Simplification of entire process lies in the fact that each measuring element $A_k$ transmits its own data to the measuring element $A_{k-1}$ and receives data from the measuring element $A_{k+1}$. The process repeats until the measuring element $A_1$ transmits N data packages to the control unit. It is preferably utilized that the sent data include information about the patient's vital functions.

DETAILED DESCRIPTION OF EXEMPLARY EMBODIMENTS

Figure 1:
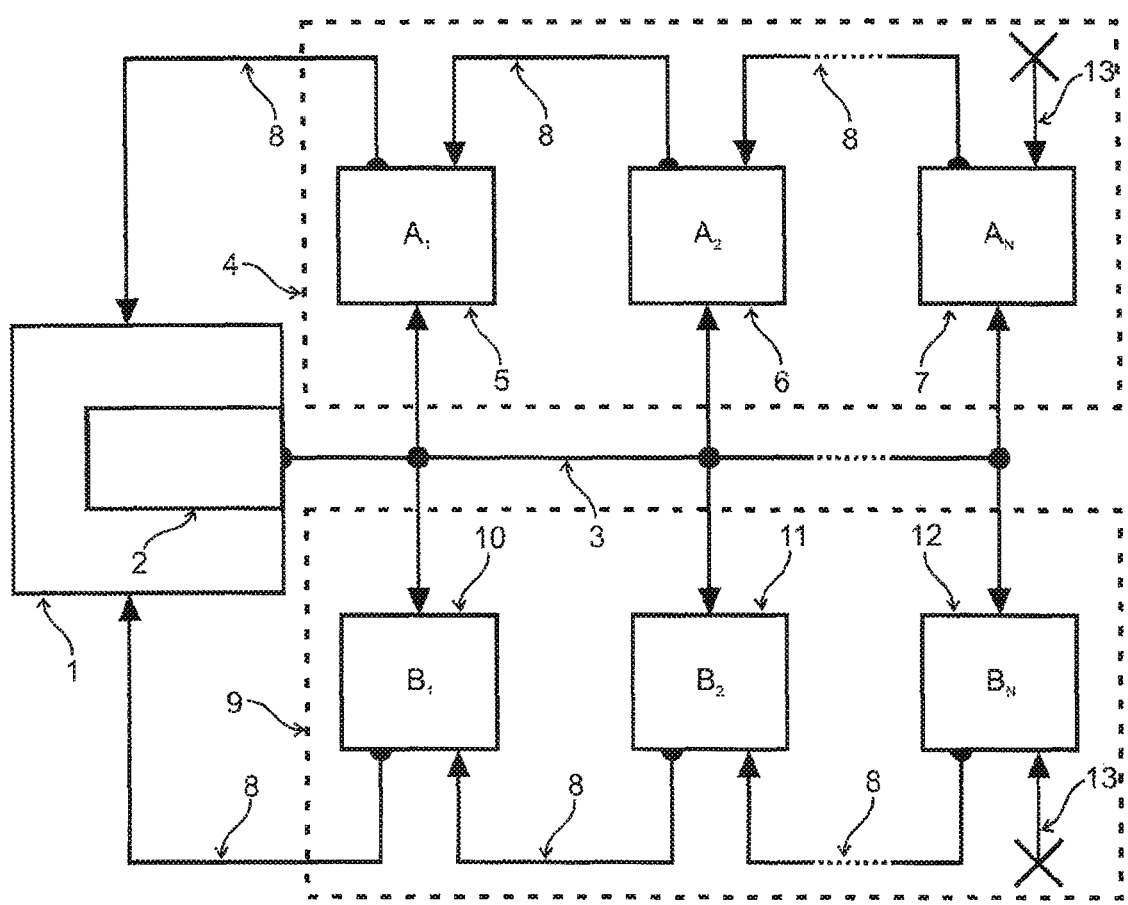
FIG. 1 is a schematic view of two chains of medical data collection system.

FIG. 1 is a schematic view of the medical data collection system. The medical data collection system consists of a control unit 1, a first chain 4 and a second chain 9. The control unit 1 further consists of a trigger 2. The trigger 2 is a unit responsible for providing a time-synchronizing pulse. The trigger 2 can be provided as a single circuit or be a software part of the control unit 1. The time-synchronizing pulse is transmitted via trigger signal path 3, with the trigger being connected to each measuring element $A_k$, $B_k$ in the first chain 4 and in the second chain 9. This arrangement allows to synchronize all measuring elements $A_N$, $B_N$ to one given time. The number of measuring elements is not limited in any way, the measuring elements are in the following description specified by indices of (1; 2; . . . ; N−1; N) series where N is the number of measuring elements connected in series, wherein the indices are assigned to the measuring elements in the direction of connection from the closest to the most distant from the control unit 1. The index k is used for the current arbitrary measuring element belonging to the set of measuring elements <1; N>.

Measuring elements $A_N$, $B_N$ are independent from each other. However, all measuring elements $A_N$ in the first chain 4 are connected to series circuit (or more preciously to the daisy chain network/scheme). The measuring element $A_N$ 7 is connected to the measuring element $A_{N-1}$ via the data signal path 8 and the measuring element $A_{N-1}$ is connected to the $A_{N-2}$ via the data signal path a. Such connection continues through each measuring element $A_k$. At the end, the measuring element $A_2$ 6 is connected to the measuring element $A_1$ 5 via the data signal path 8 and the measuring element 5 $A_1$ is connected to the control unit 1 via the data signal path 8. Thus, the control unit 1 and the plurality of measuring elements $A_k$ form a serial connection. Such arrangement requires securing appropriate ending. An end element 13 is thus the representation of blanking of the measuring element $A_N$ 7. The measuring element $A_N$ Z only measures and transmits the data, but receives none.

Every measuring element $A_k$, $B_k$ provides data package. The idea of medical data collection system is to collect each data package from each measuring element $A_k$, $B_k$ in control unit 1. When the trigger 2 transmits the time-synchronizing pulse through the trigger signal path 3 to each measuring element $A_k$, the data collection procedure is initiated and the control unit 1 is ready to collect the data packages from the measuring element $A_1$ 5. Each measuring element $A_k$ starts to both receive and transmit the data packages. Since the measuring element $A_N$ 7 is at the beginning of the measuring element series, it does not receive any data package but immediately starts to transmit its own data package to the measuring element $A_{N-1}$. While the measuring element $A_{N-1}$ is receiving the data package from the measuring element $A_N$ 7 in the place X+1 of its data storage memory, it is simultaneously transmitting its own data package from the place X of its data storage memory to the measuring element $A_{N-2}$. Once the measuring element $A_{N-1}$ finishes the transmission of its own data package to the measuring element $A_{N-2}$ and receives the entire data package from the measuring element $A_N$ 7, it starts transmitting the data package originally from the measuring element $A_N$ 7 to the measuring element $A_{N-2}$. Each measuring element $A_k$ performs the same procedure. Thus, this cascade procedure leads to collecting of all data packages in the control unit 1.

The measuring elements $B_k$ in the second chain 9 form the same serial connection as described above. The data collection procedure is also initiated by the time-synchronizing impulse from the trigger 2 and the cascade procedure of data package collection is performed from the measuring element $B_N$ 12 via all measuring elements $B_k$ to the measuring element $B_2$ 11 and the measuring element $B_1$ 10 which finally transmits data packages to the control unit 1.

In another embodiment, each measuring element has $X_N$ places in its data storage memory. The collection of data packages proceeds in the following process. The trigger 2 transmits a time-synchronizing pulse which initiates the collection of data packages. The measuring element $A_N$ 7 transmits its data packages to the place X−1 of the data storage memory of the measuring element $A_{N-1}$. Once the measuring element $A_{N-1}$ receives the entire data package from the measuring element $A_N$ 7, it starts transmitting its own data package from the place X of its data storage memory and also the data package from the place X−1 of the data storage memory (i.e. the data package previously received from the measuring element $A_N$ 7). The transmission could be either simultaneous or step-by-step. Said transmission continues towards the measuring element $A_1$ 5 which has generally N places in the data storage memory. These N places are gradually filled by the incoming/receiving data package. In the final step, the data packages are transmitted from the measuring element $A_1$ 5 to the control unit 1.

In the preferred embodiment, the data packages should have the same size. The same size of data packages ensures optimal time of data package transmission and receiving. However, this does not limit the present invention, since it is obvious to the person skilled in the art that the transmitting and receiving time could be optimized by utilizing additional software in each measuring element. In addition, the present embodiment is only illustrative and should not be considered the only solution of the technical problem. Person skilled in the art could implement the present invention in the range of application and thus use other embodiments such as connection of bed sensors, sensors of vital functions, bed exit sensors, brake sensors, bed tilt sensors or any other sensors relating to the medical data or condition collection sensors.

In addition, it is clear to the person skilled in the field of invention that the data collection system is not limited by two chains. It should be noted that the number of chains is not limited. Furthermore, it is obvious that in some applications, the connection via both the trigger signal path 3 and the data signal path 8 could be wireless.

In yet another embodiment, the data package could be divided into smaller entities. In such case, the receiving and transmitting of one or more parts of the data package could be performed simultaneously. The measuring element $A_k$ can receive part of the data package from the measuring element $A_{k+1}$ and in the same time transmit the received part of the data package to the measuring element $A_{k-1}$ before the whole data package of the measuring element $A_{k+1}$ is stored in the $A_k$.

Using the system described above provides other positive effects, for example the data transmitted from each measuring element do not need additional overhead data. The overhead data can be for example packet header, packet footer, packet checksum, server bits and so on. The data package can in some embodiments comprise a checksum, parity bits or cyclic redundancy checks to detect errors that occur during transmission.

This method is preferably used on measuring elements for measuring patient's vital functions such as are heartbeat, respiration, apnea, peristalsis or twitches of the patient's head related to the intracranial pressure. This data can be considered data associated with patient's vital functions.

Figure 2:
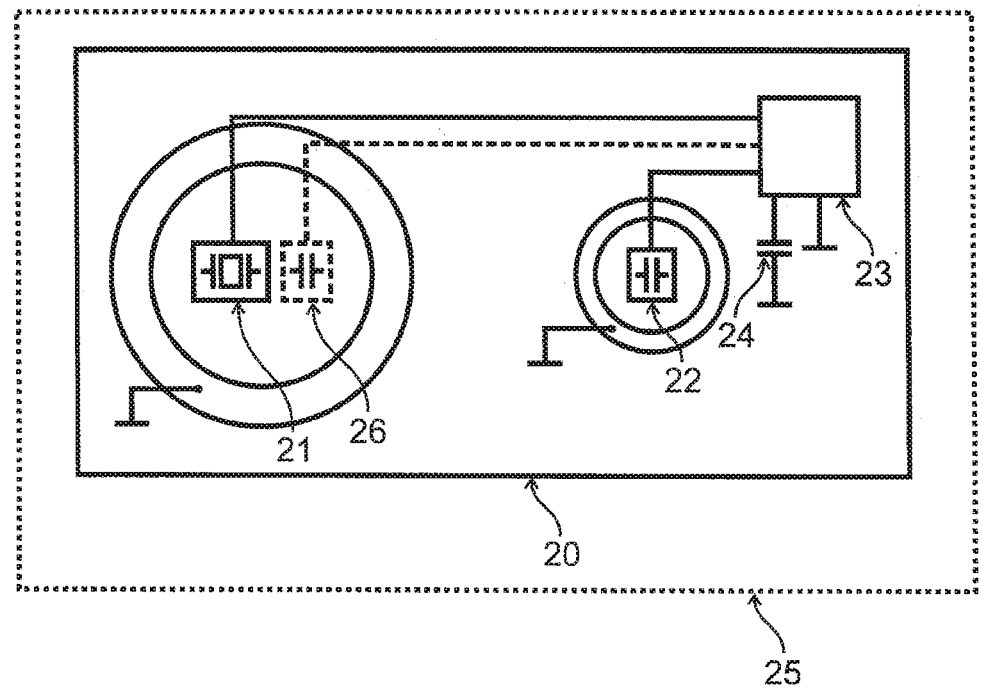
FIG. 2 shows an example of the measuring element in a top view.
Figure 3:
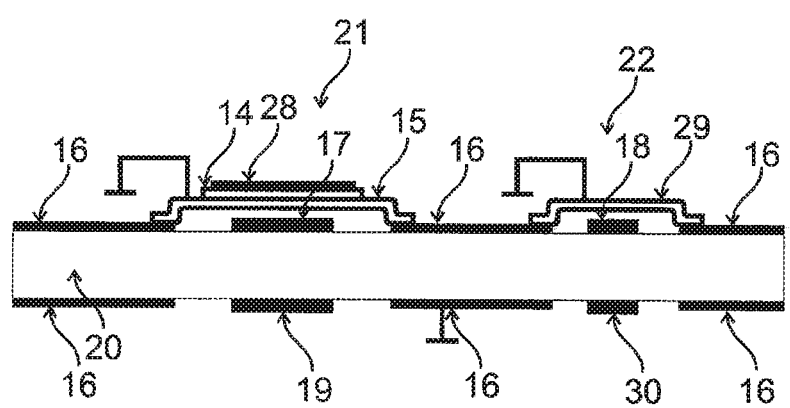
FIG. 3 shows an example of the measuring element in a side view.
Figure 4:
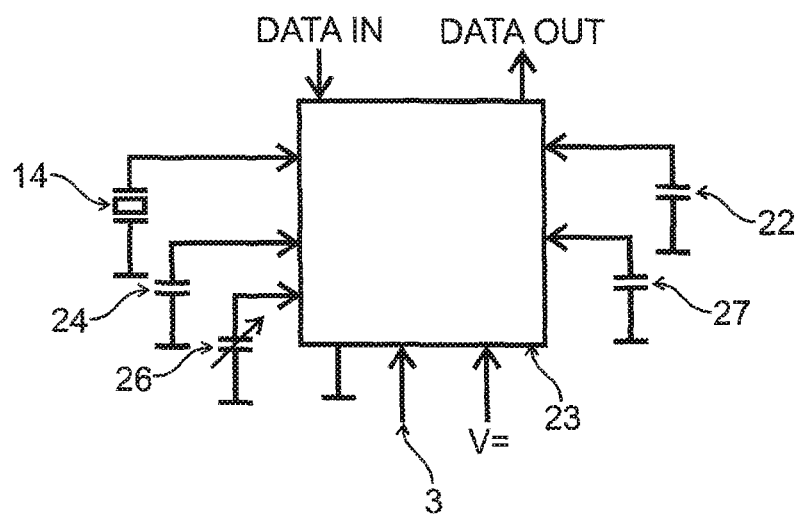
FIG. 4 is a schematic view of the measuring element.

Such system can be used with the highest efficiency on multi-sensor measuring elements, e.g., the one described in detail below. The measuring element for monitoring patient's vital functions according to FIG. 2, FIG. 3 and FIG. 4, comprising a piezoelectric transducer 21 (also known as a piezoelectric transducer), a comparator capacitor 22, a printed circuit 20 board 20, a plating 16 and a computing unit 3. The plating 16 may be, for example, of copper. The computing unit 23 of the measuring element is, according to a preferred embodiment, composed of a single processor but may also be composed of other computing parts communicating together by wire or wirelessly.

The piezoelectric transducer 21 utilized here for the purpose of measuring vital functions is a component for generating sound, namely an electro-acoustic transducer used in watches or as a siren. The piezoelectric transducer has suitable mechanical-deformative properties for measuring vital functions, which means that springs and additional members transferring their deformations caused by movements associated with patient's vital functions to the measuring element are not necessary. Thereby low production costs, higher measuring accuracy, and simplicity of the entire measuring element 5 are achieved. A semiconductor component and a circuit utilized for measuring capacity in touchscreen displays (charge transfer technology/method) are utilized in measuring capacity with this component and another measuring (static) electrode 17. A specific exemplary embodiment is described below.

In the exemplary embodiment, the measuring element 25 is on the side of the piezoelectric transducer 8 covered by, for example, a plastic diaphragm which protects the measuring element 25 against water and dust and at the same time also removes the mechanical resonance oscillation of the measuring element 25. The measuring element 22 is on the side opposite of the piezoelectric transducer 21 covered by for example plastic foil which ensures the minimum height of the entire measuring element 25. The plastic film may be replaced by any flexible or movable cover which ensures the transfer of forces to the piezoelectric transducer 21 without its stiffness significantly affecting the resulting force being transmitted to the piezoelectric transducer 1. The measuring element 25 for monitoring patient's vital functions may be adapted for insertion into the pad. The pad can be stored, for example, between the mattress and the bed frame, in the mattress or between the mattress and the patient's body. The measuring element may also be adapted for a direct placement on the bed frame and for detachable locking, for example, with a riveting knob.

The piezoelectric transducer 21 consists of the piezoelectric element 14 made out of piezoceramics, the first electrode 28 and the second electrode 15. Piezoceramics are for example piezoceramic materials based on lead zirconate titanate [Pb[Zr$_x$Ti$_{1-x}$]O$_3$ with $0 \leq x \leq 1$] or sodium bismuth titanate [NaBi(TiO$_3$)$_2$] or other piezoceramic material. By using such material, the required electromechanical properties are achieved, namely generation of charge in range of 130-930 pC/N. The piezoelectric element 14 is located between the first electrode 28 made, for example, out of silver, optionally from alloys with similar electrical properties, and the second electrode 15. The piezoelectric transducer 21 may have different shapes, such as a shape of circle, a triangle, square, or other shapes. A preferred shape is the circular shape, which ensures the most uniform decomposition of forces. The shape of the piezoelectric transducer 21 is usually a circular shape delimited in its height dimension by two parallel planes. Preferably, form modification of the piezoelectric transducer 21 can be utilized, when its center is pressed in the direction of axis perpendicular to one of the delimiting planes and a board-like shape emerges, where the center is located in one plane and the borders of the piezoelectric transducer 21 lie in the parallel way. The board-like shape is best illustrated by the shape of the second electrode 15 (or the entire piezoelectric transducer 21) in FIG. 3. The second electrode 15 may be made of brass, aluminum, copper or another metallic material. The locations of the electrodes are interchangeable, it is essential that the piezoelectric element 21 is positioned in the middle between them. The second electrode 15 may have a circular or optionally board-like shape. Alternatively, the second electrode may have the shape of ellipse, polygon, most frequently of rectangle, square, or another shape. Shape of the second electrode 15 is preferably derived from the shape of the piezoelectric transducer 21. The second electrode 15 is flat and its surface is in a rest position approximately parallel to the piezoelectric element 14. The second electrode 15 is located on the plating 16 for electrical connection with the ground, which creates a firm connection with the printed circuit board 20. The second electrode 15 is connected at least in two places to cause the required deformation of the piezoelectric transducer 21. These two places may be located, for example, opposite of each other on the opposite sides of the length of the piezoelectric transducer 21. In an alternative embodiment, the attachment can be provided so that that the first electrode 28 is located on the plating 16 and thereby the piezoelectric transducer 21 is connected with the printed circuit board 20. In a preferred embodiment, the second electrode 15 is connected in at least three places adjoining the printed circuit board 20 to provide greater stability and better course of deformation of the piezoelectric transducer 21. Preferably, these places are in the piezoelectric transducer with circular shape positioned so that they create a triangle when connected. Alternatively, the piezoelectric transducer 21 may be connected to any fixed board in this way, but by connecting to the printed circuit board 20, the dimensions of the entire measuring element 25 are minimized. The measuring capacitor 26 consists of the second electrode 15 and the measuring electrode 17. The measuring electrode 17 is connected with the printed circuit board 20 and forms electrode with higher electrical potential. The dielectric of the measuring capacitor 26 is formed by an air gap. On the opposite side of the printed circuit board 20 opposite of the measuring electrode 17 there is the shielding electrode 19 of the measuring capacitor 26. The shielding electrode 19 of the measuring capacitor 26 has the same electrical potential as the measuring electrode 17 and together they can form a shielding capacitor 27 which provides resistance to external influences for example by the approximation of metal material. In some cases, two or more piezoelectric transducers 21 may be located on one circuit board 20.

The comparator capacitor 22 consists of the first comparator electrode 29, the first comparator electrode 29 can be made, for example, of brass, aluminum, copper. The first comparator electrode 29 is located on the plating 16 for electrical connection with the ground. The comparator capacitor 22 further consists of a second comparator electrode 18. The second comparator electrode 18 is located on the printed circuit board 20 and forms an electrode with higher electrical potential. The dielectric of the comparator capacitor 22 is formed by an air gap. On the opposite side of the printed circuit board 20 opposite of the second comparator electrode 18 is located the shielding electrode 30 of the comparator capacitor 22. The shielding electrode 30 of the comparator capacitor 22 has the same electrical potential as the comparator electrode 18 and together they can form ta shielding capacitor 27 which provides resistance to external influences for example by the approximation of metal material.

The computing unit 23 of the measuring element combines piezoelectric voltage measurement and capacity measurement functions, for example, by means of charge transfer technology. The piezoelectric element 14 is connected to the computing unit 23 of the measuring element through a charge amplifier. Furthermore, the measuring capacitor 26, the comparator capacitor 22, the shielding capacitor 27 and the sampling capacitor 24 are connected to the computing unit 23 of the measuring element. The use of the measuring capacitor 26 and the comparator capacitor 22 causes resistance to changes in the measuring conditions such as temperature or humidity.

Furthermore, a method for monitoring patient's vital functions according to the above-mentioned exemplary embodiment is described. Heartbeat, breath and other vital functions of the patient, for example peristalsis, generate forces transmitted to the measuring element 25 for monitoring patient's vital functions. With respect to the construction of the measuring element 25, it is ensured that the vital functions of the patient are measurable without the need for permanent connection of the measuring element 25 with the patient's body, for example by means of gluing or implanting. The measuring element 25 is capable of measuring patient's vital functions in contact with the skin of the patient, but also in contact with patients clothing, mediated through the mattress on which the patient is placed, or through the pad in which the measuring element 25 for monitoring vital functions may be located. The measuring capacitor 26 and the comparator capacitor 22 are used to measure slowly changing forces generated by, for example, breathing. During breathing, due to the applied forces, deflection of the central portion of the second electrode 15 (and therefore to the entire piezoelectric transducer 21) occurs, and thus also change in the air gap between the second electrode 15 and the measuring electrode 17. Due to the construction where the piezoelectric transducer 21 is attached to the board by one of the electrodes, a non-mediated deflection of the piezoelectric transducer 21 without the need for additional force transmitting components is enabled. The size of the air gap between the first comparator electrode 29 and the second comparator electrode 18 is independent of the action of the forces. The change in the capacity of the measuring capacitor 26 is dependent both on the varying air gap size and on the change of permittivity of the air gap. The change in the capacity of the comparator capacitor 22 is dependent only on change in permittivity of the air gap. The capacity of the measuring capacitor 26 and the capacity of the comparator capacitor 22 ratio will remove the dependence of the capacitance change on dielectric permittivity and thereby the independence of changing the measuring conditions.

Capacity changes are evaluated for example by charge transfer technology. The charge transfer technology operates on the principle of charging the capacitor and subsequent transfer of the accumulated charge into the sampling capacitor 24, wherein the number of accumulated charge transfers into the sampling capacitor is counted, until the voltage at the sampling capacitor 24 reaches the same value as the stable reference voltage. It is clear to a person skilled in the art that other methods of measuring capacity can be utilized, for example, the resonance method. In order to measure fast-changing forces caused for example by pulse, a direct piezoelectric effect of the piezoelectric material is used, where by deformation of the piezoelectric material due to external forces, a charge which is through the charge amplifier transferred to the computing unit 23 of the measuring element is generated where the voltage is evaluated. The output data are then transmitted via the data wire 8 to the control unit 1. The computing unit 23 of the measuring element can be provided as a microprocessor, its location on the printed circuit board 20 ensures a protection of the signal because the distance of the transmitted non-digital signal is very small.

LIST OF REFERENCE SIGNS

1 . . . main control unit
2 . . . trigger
3 . . . trigger signal path
4 . . . first chain
5 . . . measuring element A1
6 . . . measuring element A2
7 . . . measuring element AN
8 . . . data signal path
9 . . . second chain
10 . . . measuring element B1
11 . . . measuring element B2
12 . . . measuring element BN
13 . . . end element
14 . . . piezoelectric element
15 . . . second electrode
16 . . . plating
17 . . . measuring electrode
18 . . . second comparator electrode
19 . . . shielding electrode of the measuring capacitor
20 . . . printed circuit board
21 . . . piezoelectric transducer
22 . . . comparator capacitor
23 . . . computing unit of the measuring element
24 . . . sampling capacitor
25 . . . measuring element
26 . . . measuring capacitor
27 . . . shielding capacitor
28 . . . first electrode
29 . . . first comparator electrode
30 . . . shielding electrode of the comparator capacitor

The invention claimed is:

1. A medical data collection system comprising:
a control unit, and
a plurality of measuring elements separate from the control unit, wherein the measuring elements are connected in series through a first data signal path, wherein the control unit comprises a trigger and the trigger is connected to each measuring element via a trigger signal path, which is independent of the first data signal path, wherein the trigger provides a trigger impulse to effect simultaneous transmission of data packages from the measuring elements to adjacent ones of the measuring elements throughout the first data signal path.

2. The medical data collection system according to claim 1, wherein each of the plurality of measuring elements comprises a piezoelectric and capacity sensor of vital functions.

3. The medical data collection system according to claim 2, wherein the patient vital functions are selected from a group of vital functions comprising heartbeat, respiration, apnea, peristalsis and twitches of a patient's head related to intracranial pressure.

4. The medical data collection system according to claim 1, wherein each of the plurality of measuring elements comprises a computing unit for processing signals for the measuring elements.

5. The medical data collection system according to claim 1, wherein the plurality of measuring elements is a first chain of measuring elements, the system further comprising a second chain of measuring elements independent of the first chain.

6. The medical data collection system according to claim 5, wherein the measuring elements of the second chain are connected in series through a second data signal path independent of the first data signal path.

7. The medical data collection system according to claim 1, wherein the measuring elements are non-implantable.

8. The medical data collection system according to claim 1, wherein the trigger is provided as a single circuit or a software part of the control unit.

9. The medical data collection system according to claim 1, wherein the data packages are transmitted through the measuring elements in a cascading manner.

10. The medical data collection system according to claim 1, wherein the data packages are received and transmitted through one or more of the measuring elements.

11. The medical data collection system according to claim 10, wherein receiving and transmitting of one or more parts of one of the data packages is performed simultaneously.

12. The medical data collection system according to claim 11, wherein at least one of the measuring elements receives part of the data package from another one of the measuring elements and at the same time, transmits a previously received part of the data package to another one of the measuring elements.

13. The medical data collection system according to claim 1, wherein all the data packages are the same size to ensure optimal transmission of the data packages.

14. The medical data collection system according to claim 1, wherein one or both of the data signal path and the trigger path are wireless.

15. The medical data collection system according to claim 1, wherein the measuring elements are adapted to be placed directly on a bed frame or inserted into a pad for placement between a mattress and the bed frame, or in the mattress, or between the mattress and the patient.

16. The medical data collection system according to claim 1, wherein one or more of the measuring elements has data storage memory for collecting the data package from at least one of the other measuring elements.

17. A method of medical data collection in a data collection system comprising a plurality of measuring elements $A_k$, wherein the plurality of measuring elements $A_k$ are connected in series through a data signal path, wherein a control unit comprises a trigger, wherein the trigger is connected to each of the plurality of measuring elements $A_k$ through a trigger signal path, and wherein the method comprises the following steps:
  a) the trigger initiating the data collection by transmitting a time-synchronizing impulse to each of the plurality of measuring elements $A_k$, wherein k is an interval [1,N],
  b) a measuring element $A_N$ transmitting a data package to a measuring element $A_{N-1}$,
  c) measuring elements $A_2$ to $A_{N-1}$ simultaneously receiving data packages from measuring elements $A_{k+1}$ and transmitting data packages to measuring elements $A_{k-1}$, and
  d) a measuring element $A_1$ receiving a data package from the measuring element $A_2$ and transmitting a data package to the control unit.

18. The method of medical data collection in a data collection system according to claim 17, further comprising the steps of:
  measuring elements $A_2$ to $A_{N-2}$ simultaneously receiving data packages from a measuring element $A_{k+2}$ and transmit previously received data packages to the measuring element $A_{k-1}$,
  the measuring element $A_1$ receiving a data package from the measuring element $A_2$ and transmitting a previously received data package to the control unit,
  a cascade of receiving and transmitting data packages continuing until the data package from the measuring element $A_N$ is transmitted to the control unit by the measuring element $A_1$.

19. The method of medical data collection in a data collection system according to claim 17, wherein the transmitted data includes information about a patient's vital functions.

20. A medical data collection system comprising:
  a control unit, and
  a plurality of multi-sensor non-implantable measuring elements separate from the control until, each measuring element comprising a piezoelectric transducer for measuring slow changes in vital functions of a patient and a comparator capacitor for measuring fast changes in the vital functions without need for a physical connection to the patient, wherein the measuring elements are connected in series through a data signal path, wherein the control unit comprises a trigger and the trigger is connected to each measuring element via a trigger signal path, which is independent of the data signal path, to simultaneously transmit a data package from each one of the measuring elements to an adjacent one of the measuring elements all at one time through the data signal path based on a synchronized trigger impulse from the trigger, and wherein the trigger path carries only the trigger impulse.

21. A method of medical data collection in a data collection system comprising a control unit and a plurality of measuring elements, wherein the plurality of measuring elements are connected in series through a data signal path, wherein the control unit comprises a trigger and the trigger is connected to each of the plurality of measuring elements via a trigger signal path, which is independent of the data signal path, to simultaneously transmit a data package from the plurality of measuring elements through the data signal path based on a synchronized trigger impulse from the trigger, and wherein the method comprises the following steps:
  a) initiating the data collection from the plurality of measuring elements by transmitting a first synchronized trigger impulse from the trigger to the plurality of measuring elements,
  b) transmitting a first data package from at least one of the plurality of measuring elements to a successive one of the plurality of measuring elements by transmitting a second synchronized trigger impulse from the trigger to the plurality of measuring elements,
  c) repeating the transmitting step until the first data package is received by a closest one of the measuring elements to the control unit, and
  d) transmitting the data package from the closest one of the measuring elements to the control unit to the control unit.

22. The method of medical data collection in a data collection system according to claim 21, wherein the plurality of measuring elements simultaneously receive data packages from a preceding one of the measuring elements and transmit previously received data packages to a successive one of the measuring elements, and wherein a cascade of receiving and transmitting data packages continues until the data package from the first data package is transmitted to the control unit by the closest one of the measuring elements to the control unit.

* * * * *